United States Patent [19]

Renga

[11] 4,242,285
[45] Dec. 30, 1980

[54] NOVEL 2,6-DINITROPHENYL SELENIUM COMPOUNDS AND THEIR USE AS EPOXIDATION CATALYSTS

[75] Inventor: James M. Renga, Midland, Mich.
[73] Assignee: The Dow Chemical Company, Midland, Mich.
[21] Appl. No.: 21,272
[22] Filed: Mar. 16, 1979
[51] Int. Cl.$^3$ ............... C07C 163/00; C07D 301/12; B01J 27/02
[52] U.S. Cl. ..................... 260/348.31; 252/439; 260/550
[58] Field of Search ............ 260/607 R, 454, 348.31, 260/453 R, 543 R, 545 R, 500.5 R

[56] References Cited

U.S. PATENT DOCUMENTS

| | | | |
|---|---|---|---|
| 3,806,467 | 4/1974 | Watanabe et al. | 252/429 R |
| 3,953,480 | 4/1976 | Delavarenne et al. | 260/348.5 L |
| 3,993,673 | 11/1976 | McMullen | 260/348.5 L |

FOREIGN PATENT DOCUMENTS 2605041  8/1976  Fed. Rep. of Germany.

OTHER PUBLICATIONS

P. Grieco et al, J. Org. Chem., 42, No. 11, pp. 2034–2036 (1977), Organoselenium Chemistry, Epoxidation of Olefins with Benzeneselenic Acid and $H_2O_2$.
T. Hori et al, J. Org. Chem., 43, No. 9, pp. 1689–1696 (1978), Synthetic Applications of Arylselenic and Arylseleninic Acids, Conversion of Olefins to Allylic Alcohols and Epoxides.
E. Jeney et al., Chem. Abst. 55:16277b (1959), Bacteriostatic Action of Organic Selenocyanates.
D. Garratt et al, Chem. Abst. 82:139568c (1975), Addition of Arylselenium Trichlorides vs. Areneselenyl Chlorides to cis–and trans–1–phenylpropene.
H. Reich et al., Synthesis, No. 4, pp. 299–301 (1978), Seleninic Acids as Catalysts for Oxidation of Olefins and Sulfides using $H_2O_2$.
N. Sonoda et al., Bull. Chem. Soc. Japan, 38, pp. 958–961 (1965).
M. Mugdan et al., J. Chem. Soc., pp. 2988–3000 (1949).
T. Austad, Chem. Abstr. 87:21898k (1977).

*Primary Examiner*—Donald G. Daus
*Assistant Examiner*—M. C. Eakin
*Attorney, Agent, or Firm*—Michael L. Glenn

[57] ABSTRACT

Novel unsubstituted and 4-substituted, 2,6-dinitrophenyl seleninic acids, selenium halides and diselenides are described. The above-described selenium compounds are particularly useful to catalyze the oxidation of olefins to the corresponding epoxide in the presence of hydrogen peroxide.

11 Claims, No Drawings

NOVEL 2,6-DINITROPHENYL SELENIUM COMPOUNDS AND THEIR USE AS EPOXIDATION CATALYSTS

BACKGROUND OF THE INVENTION

This invention pertains to novel 2,6-dinitrophenyl seleninic acids, selenium halides and diselenides. More particularly, this invention relates to a process for utilizing these novel selenium compounds to catalyze the epoxidation of olefins.

Epoxides are utilized in the chemical industry as intermediates in the preparation of urethanes, glycol solvents, coating compositions, surfactants, plasticizers and many other products. The most widely employed commercial procedure for preparing epoxides involves the oxidation of a double bond with chlorine to form the chlorohydrin, followed by a base-promoted ring closure to form the epoxide. The principal disadvantage of this process is the simultaneous production of a stoichiometric quantity of a chloride salt as the by-product.

A silver-based catalyst can be utilized with molecular oxygen to epoxidize ethylene in the vapor phase. However, this technique is not generally applicable to substituted olefins due to a lack of selectivity and the formation of by-products.

U.S. Pat. No. 3,351,635 discloses a two-step process in which a hydrocarbon, such as isopropyl benzene or isobutane, is first oxidized by air to the corresponding hydroperoxide. The hydroperoxide intermediate is then reacted with the olefin in the presence of vanadium, molybdenum or tungsten. However, this process suffers from the disadvantage that a stoichiometric amount of alcohol is generated along with the epoxide.

The use of a variety of organometallic compounds as catalysts for epoxidation of olefins with hydrogen peroxide has been taught. U.S. Pat. Nos. 3,993,673 and 3,953,480 disclose the use of organometallic catalysts of lead, antimony, bismuth and arsenic. However, these organometallic catalysts are not completely satisfactory, because they do not exhibit sustained, high catalytic activity.

SUMMARY OF THE INVENTION

A novel group of 2,6-dinitrophenyl selenium compounds has now been discovered, which are catalysts or catalyst precursors for the epoxidation of olefins with hydrogen peroxide. The novel 2,6-dinitrophenyl selenium compounds correspond to formula I or II

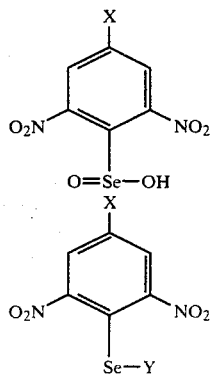

wherein in each of the above formulae, X is selected from the group consisting of hydrogen, trifluoromethyl, trichloromethyl, nitro, chloro and bromo moieties; and in Formula II, Y is cyanide, bromine, chlorine or a monovalent group corresponding to the formula

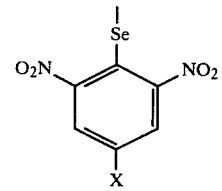

wherein X has the aforesaid meaning.

The novel catalysts are surprisingly effective in selectively catalyzing the desired epoxidation of alkenes. Unexpectedly high rates of epoxidation are achieved with the above-described catalysts. These novel compounds also possess utility as fungicides and/or bacteriacides.

DETAILED DESCRIPTION OF THE INVENTION

The Novel Catalysts

The selenium compounds which we have found to be useful as catalysts for epoxidation are unsubstituted and 4-substituted, 2,6-dinitrophenyl seleninic acids, selenium halides and diselenides. The substituent in the 4-position of the phenyl group(s) is preferably hydrogen or a nitro moiety. The 2,6-dinitrophenyl seleninic acids are preferred as catalysts, because these acids are the immediate precursor to the activated species which participate in the epoxidation reaction. The seleninic acid can also be formed in situ, as by the reaction of selenium halides or diselenides with hydrogen peroxides. The in situ formation of the seleninic acid, however, requires a stoichiometric equivalent of hydrogen peroxide, which then of course is not available for the epoxidation reaction.

Preparation of the Catalysts

The 2,6-dinitrophenyl diselenides can be readily prepared in a three-step process. In step 1, an alkali metal cyanide is reacted with an equivalent of elemental selenium in an inert medium to yield the alkali metal selenocyanate. In the second step, the alkali metal selenocyanate is reacted in an inert solvent with a 2,6-dinitrochlorobenzene bearing the desired substituent in the 4-position to prepare the corresponding 2,6-dinitrophenyl selenocyanate. Finally, the 2,6-dinitrophenyl selenocyanate compound is reacted with a mild base, such as ammonia, in an inert solvent to prepare the corresponding diselenide.

By appropriate selection of the solvent in the third step, the diselenide product can be readily recovered as a precipitate. Desirably, the solvent in each of the three steps is the same, so as to eliminate steps in which the intermediate products are recovered. Representative inert solvents operable in this process include lower alkanols, such as methanol, ethanol and the like; chlorinated lower alkanes, such as methylene chloride and the like; and highly polar hydrocarbons, such as N,N-dimethylformamide, dimethylsulfoxide and the like. Illustrative mild bases operable in step 3 of the process include ammonia and primary and secondary amines.

A 2,6-dinitrophenyl selenium halide is prepared by reacting a 2,6-dinitrophenyl selenocyanate, prepared in the manner previously described, with molecular chlorine or bromine in an inert solvent. The selenium halide product can be readily recovered by distillation at reduced pressure to remove the solvent.

A 2,6-dinitrophenyl seleninic acid is readily prepared by treating the corresponding diselenide or selenium halide with an oxidizing agent in an inert solvent. Conveniently, hydrogen peroxide is employed as the oxidizing agent and a small amount of trifluoroacetic acid is optionally used to promote the oxidation.

The foregoing preferred methods of preparing the catalysts are generally known in the art. Other operable processes are also known in the art and can alternatively be employed to prepare the described selenium compounds. See e.g., Campbell et al., *Chem. Rev.*, 50, p. 279 (1952).

Preparation of Epoxides

The epoxidation of olefins with the described selenium catalysts is conveniently carried out in a liquid mixture of the olefin and hydrogen peroxide. An inert organic solvent can be used as necessary to establish the liquid phase. However, the preferred reaction medium is a two-phase system consisting essentially of an organic solvent containing the olefin (and the epoxide product when formed) and an aqueous hydrogen peroxide phase. It is preferred that the organic solvent is water-immiscible to minimize the hydrolysis of the epoxide to the corresponding glycol. Representative organic solvents operable in the process include chlorinated alkanes, such as chloroform, carbon tetrachloride, 1,2-dichloroethane, 1,1,2-trichloroethane and the like; aromatic carbocyclic compounds, such as benzene, chlorobenzene and the like; heterocyclic compounds, such as tetrahydrofuran, pyridine and the like; olefins, such as those to be epoxidized and miscible mixtures of the foregoing.

The minimum quantity of solvent in the reaction medium is determined by the amount needed to maintain the liquid phase. Generally, the amount is in the range of about 5 percent by volume to about 95 percent by volume based on the volume of the total reaction mixture including olefin, hydrogen peroxide solution, catalyst and solvent. It is preferably in the range of about 25 percent by volume to about 75 percent by volume. Other quantities of solvent can be used, however, so long as there is a sufficient amount to maintain the reaction in the liquid phase.

The hydrogen peroxide is desirably employed in this process in a ratio of from about 0.1 to about 2 moles of the peroxide per mole of olefin. The foregoing ratio can operably be much less than 0.1 mole of peroxide per mole of olefin, if the olefin is utilized as the organic solvent. More than 2 equivalents of $H_2O_2$ per equivalent of olefin are operable but not desirable for reasons of economy. Of course, when less than one equivalent of hydrogen peroxide is employed, only part of the olefin present will be epoxidized at equilibrium. Preferably, the hydrogen peroxide is present in a ratio of from about 1 to about 1.2 moles of hydrogen peroxide per mole of the olefin to be epoxidized. If the catalyst is introduced to the reaction medium as a diselenide or selenium halide, then additional hydrogen peroxide should be present in a quantity sufficient to oxidize these selenium compounds to the corresponding seleninic acid. In the preferred biphasic reaction medium, from about 30 to greater than 90 weight percent hydrogen peroxide in the aqueous solution is advantageously employed.

The olefin reactant can be broadly defined as an epoxidizable olefinically unsaturated hydrocarbon. The olefin can also be cyclic or acyclic. It has been found that those olefins bearing at least one and preferably two or more inert, electron-donating substituents in α-positions to the olefinic carbons, are generally more readily epoxidized than like olefins bearing hydrogen substituents in these positions. Representative substituents, which are more electron-donative than hydrogen, include alkyl, aryl and oxyalkyl. Propylene, butene-1, butene-2, isobutylene, pentene-1, hexene-1, pentene-2, octene-1, cyclopentene, cyclohexene, cyclooctene, and 1,2-diphenylethylene are illustrative epoxidizable olefins. Other epoxidizable olefins are described in U.S. Pat. No. 3,993,673. It has been observed that the described catalysts are not effective with ethylene.

The olefin can be epoxidized in a continuous or batchwise process. Generally, some form of agitation is desirable to insure intimate contact of the reactants and catalyst during the epoxidation reaction.

A catalytically active amount of catalyst is required. The upper limit of the selenium catalyst loading is set primarily for economic reasons, as even equimolar amounts of catalyst and hydrogen peroxide are operable. Preferably, the selenium-based catalyst is employed in a ratio of from about 0.001 to about 10, more preferably about 0.01 to about 1, mole percent of catalyst based on the moles of hydrogen peroxide present at the beginning of the reaction.

The ratios of olefin and hydrogen peroxide can be kept fairly constant by the use of a continuous process and by analyzing the outlet ratio and adjusting the feed ratio. In a backmixed reactor, the feed is adjusted until the outlet ratio is within the prescribed range. Where two or more reactors are used in series or the reactor is tubular with multi-point injection, the reactions taking place are considered to be a series of batch reactions and are carefully monitored to insure for the most part that the molar ratio in any one reaction is not permitted to go below or rise above a desired range.

The reaction can be conducted in an atmosphere of air or oxygen since the olefin selectively reacts with the hydrogen peroxide in preference to the molecular oxygen; however, the reaction is preferably conducted in an essentially oxygen-free atmosphere. This is provided by conventional means, e.g., by using an inert gas such as nitrogen, argon, or helium as the atmosphere in which the process is carried out.

The pressure is generally in the range of about atmospheric pressure to about 1500 psia. Pressure is selected so as to maintain the liquid phase at the reaction temperature.

The temperature of the reaction can be in the range of about 0° C. to about 100° C. and is preferably in the range of about 25° C. to about 80° C. Lower temperatures result in decreased reaction rates.

The time of the reaction is simply that in which one or the other reactants, usually the hydrogen peroxide, is used up. This is applicable in batch and semi-continuous processes to which subject process can be applied. In continuous processes, which are preferred for commercial use, the reactants are continuously fed so that time of reaction is merely the measure of the length of each cycle.

The conversion of hydrogen peroxide to the epoxide is generally quite efficient, with conversions ranging from 75 to 100 mole percent being observed when a stoichiometric equivalent of hydrogen peroxide is employed. Recovery, separation and analysis of products and unreacted materials are accomplished by conventional means.

The following examples illustrate the invention. Percentages and parts are by weight unless otherwise specified.

EXAMPLE 1

In a closed reaction vessel 6.4 grams (0.055 mole) of nitrosylborofluoride in 100 milliliters (ml) of dry acetone are added dropwise over a 30-minute period at −20° C. to a stirred solution of 9.2 grams (0.05 mole) of 2,6-dinitroaniline in 100 ml of acetone under a nitrogen atmosphere. The reaction medium is stirred for an additional 30 minutes and then 200 ml of chloroform are added at −20° C. The resulting diazonium salt precipitate is collected by filtration, washed with 50 ml of diethyl ether and dried to a weight of 8.45 grams (0.03 mole).

In a closed reaction vessel under a nitrogen atmosphere, 4.75 grams (0.033 mole) of potassium selenocyanate in 15 ml of acetone are added dropwise over a 30-minute period at −20° C. to a stirred solution of 8.45 grams of the diazonium salt product in 100 ml of acetone. The reaction medium is stirred for an additional 30 minutes and then 200 grams of crushed ice are introduced. The resulting precipitate is collected by filtration, washed with 100 ml of water, recrystallized in 75 ml of ethanol and dried to a weight of 5.4 grams. The brown, crystalline product is identified by proton magnetic resonance, elemental analysis and other conventional methods of analysis as 2,6-dinitrophenyl selenocyanate. The melting point of the product is 91°–92° C. The yield of the product is 66 mole percent based on the diazonium salt.

EXAMPLE 2

Ammonia is sparged through a solution of 1.36 grams (0.005 mole) of 2,6-dinitrophenyl selenocyanate in 15 ml of ethanol at 20° C. for one hour. The reaction medium is then stirred for an additional hour at 50° C. The resulting precipitate is collected by filtration, washed with 30 ml of cold ethanol and dried to a weight of 0.8 gram. The crystalline product is identified by proton magnetic resonance, elemental analysis and other conventional methods of analysis as 2,6-dinitrophenyl diselenide.

EXAMPLE 3

In a closed reaction vessel under a nitrogen atmosphere, 1.21 ml (0.022 mole) of bromine are added to 2.72 grams (0.01 mole) of 2,6-dinitrophenyl selenocyanate in 40 ml of chloroform at 20° C. over a period of one hour. The reaction mixture is stirred for 18 hours and then the volatile solvent and excess bromine are removed by distillation. The red, solid product is recrystallized from 50 ml of a 50:50 mixture of chloroform and hexane to give 3.13 grams. The product is identified by proton magnetic resonance and elemental analysis as 2,6-dinitrophenyl selenium bromide. The melting point of the product is 89°–91° C. The yield of the product is 93 mole percent based on the selenocyanate.

EXAMPLES 4–5

In a reaction vessel equipped with a stirrer, a condenser and a means for measuring temperature, 0.005 mole of cyclohexene in 2.5 ml of methylene chloride is added over a 5-minute period to a stirred reaction medium consisting of $5 \times 10^{-5}$ mole of 2,6-dinitrophenyl selenium bromide and 0.006 mole of aqueous hydrogen peroxide at 25° C. The hydrogen peroxide is present in 50 percent and 95 percent aqueous solutions in Examples 4 and 5, respectively. The progress of the reaction is monitored by conventional gas phase chromatographic analysis of the organic phase with an internal mesitylene standard. After about 50 percent of the cyclohexene has been converted to the corresponding epoxide, the reaction rate of 25° C. is calculated. The rate constants observed in Examples 4 and 5, respectively, are $6 \times 10^{-4}$ and $14.5 \times 10^{-4}$ per second. In comparison, the rate of reaction observed in a similar epoxidation reaction with a 2-nitrophenyl-seleninic acid catalyst (not embodying the instant invention) is at least an order of magnitude slower.

EXAMPLES 6–14

In a reaction vessel equipped with a stirrer, a condenser and a means for measuring temperature, 0.04 mole of an olefin in 20 ml of methylene chloride is added over a 5-minute period to a stirred reaction medium consisting of $4 \times 10^{-4}$ mole of 2,6-dinitrophenyl selenium bromide and 0.048 mole of hydrogen peroxide as a 95 percent solution in water. The reaction medium is stirred for periods of 2 to 4 hours at 40° C. The yield of epoxide is determined by a conventional gas phase chromatographic analysis of the organic phase with an internal mesitylene standard. In some instances an isolated yield is also determined by first separating the organic from the aqueous phase and then isolating the epoxide by fractional distillation. The olefin reactant, time of reaction and molar yield of olefin, epoxide and glycol based on initial olefin reactant are tabulated in Table I.

TABLE I

| Ex. | Olefin | Time (hours) | Yield (Mole %) | | |
|---|---|---|---|---|---|
| | | | Olefin | Epoxide | Glycol |
| 6 | 2,4,4-Trimethyl but-1-ene | 4 | 6 | 87(81)* | 2 |
| 7 | Cyclohexene | 2 | 1 | 96 | 3 |
| 8 | cis-2-Octene | 2 | NA | (88)* | NA |
| 9 | trans-Stilbene | 3 | 48 | 49 | — |
| 10 | 1-Octene | 2 | 81 | 16 | — |
| 11 | Styrene | 2 | 69 | 29 | — |
| 12 | Allyl t-butyl ether | 2 | 86 | 11 | — |
| 13 | 2-Chloro-2-methyl-prop-1-ene | 2 | 99 | 1 | — |
| 14 | Cyclohexen-3-ol | 2 | 8 | 80(75)* | — |

*Yields in parentheses are isolated yields.
N.A. - Not available.

EXAMPLE 15

In a manner similar to Example 6 with the exceptions noted herein, 0.04 mole of cyclopentene is epoxidized at 20° C. in the presence of $2 \times 10^{-4}$ mole of 2,6-dinitrophenyl selenium bromide. After 2 hours, an 81 mole percent yield of an epoxide is recovered by fractional distillation of the organic phase to isolate the epoxide.

EXAMPLE 16

In a manner similar to Example 6 with the exceptions noted herein, 0.005 mole of propylene in 2.5 ml of 1,2-dichloroethane is added to a glass ampoule containing $5 \times 10^{-5}$ mole of 2,6-dinitrophenyl selenium bromide and 0.006 mole of hydrogen peroxide as a 95 percent solution in water. The ampoule is sealed and the reaction mixture is agitated for 2 hours at 40° C. The yield of epoxide is then determined by a conventional gas phase chromatographic analysis of the organic phase with an internal mesitylene standard. The yield of the propylene oxide is 15 mole percent.

COMPARATIVE EXPERIMENT

In a manner similar to Example 6, 2,4,4-triethylbut-1-ene is epoxidized, except that a 1:1 molar ratio of olefin to hydrogen peroxide is employed with a 2,4-dinitrophenyl selenium bromide catalyst. After 22 hours of reaction the molar yield of epoxide is only about 68 percent based on the olefin reactant initially present.

What is claimed is:

1. A 2,6-dinitrophenyl selenium compound corresponding to the formula I or II

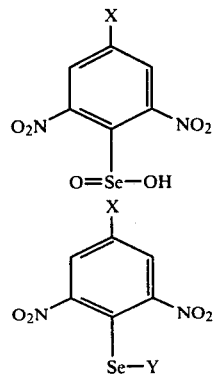

wherein in each of the above formulas, X is selected from the group consisting of hydrogen, trifluoromethyl, trichloromethyl, nitro, chloro and bromo moieties; and in Formula II, Y is bromine or chlorine.

2. The selenium compound as described in claim 1 wherein X is hydrogen or a nitro moiety.

3. The selenium compound as described in claim 2 wherein the compound corresponds to formula I.

4. A process for preparing epoxides from olefins comprising admixing an olefin bearing at least one alkyl, aryl or oxyalkyl substituent in an α-position to an olefinic carbon with hydrogen peroxide in a liquid reaction medium in the presence of an effective amount of an epoxidation catalyst prepared by introducing at least one of the compounds described in claim 1 to the reaction medium.

5. The process as described in claim 4 wherein the reaction medium comprises two phases, the olefin being present in a water-immiscible organic solvent phase and the hydrogen peroxide being present in a separate aqueous phase.

6. The process as described in claim 5 wherein the organic solvent is selected from the group consisting of chlorinated alkanes, aromatic carbocyclic compounds, heterocyclic compounds and epoxidizable olefins.

7. The process as described in claim 5 wherein about 0.1 to about 2 equivalents of hydrogen peroxide per equivalent of olefin are present in the biphasic reaction medium.

8. The process as described in claim 7 wherein the aqueous phase consists of about 30 to greater than 90 weight percent hydrogen peroxide at the beginning of the epoxidation reaction.

9. The process as described in claim 5 or 8 wherein the olefin is propylene, butene-1, butene-2, isobutylene, pentene-1, hexene-1, pentene-2, octene-1, cyclopentene, cyclohexene, cyclooctene or 1,2-diphenylethylene.

10. The selenium compound as described in claim 1 wherein Y is bromine and X is hydrogen.

11. The selenium compound as described in claim 3 wherein X is hydrogen.

* * * * *